(12) United States Patent
Xu et al.

(10) Patent No.: US 7,171,841 B2
(45) Date of Patent: Feb. 6, 2007

(54) ULTRAFAST AND ULTRASENSITIVE HYDROGEN SENSORS BASED ON SELF-ASSEMBLY MONOLAYER PROMOTED 2-DIMENSIONAL PALLADIUM NANOCLUSTERS

(75) Inventors: Tao Xu, Darien, IL (US); Michael P. Zach, Darien, IL (US); Zhili Xiao, Naperville, IL (US)

(73) Assignee: UChicago Argonne, LLC, Chicago, IL (US)

( * ) Notice: Subject to any disclaimer, the term of this patent is extended or adjusted under 35 U.S.C. 154(b) by 18 days.

(21) Appl. No.: 11/001,193

(22) Filed: Dec. 1, 2004

(65) Prior Publication Data

US 2006/0112756 A1 Jun. 1, 2006

(51) Int. Cl.
- G01N 7/00 (2006.01)
- G01N 9/00 (2006.01)
- G01N 19/10 (2006.01)
- G01N 25/00 (2006.01)

(52) U.S. Cl. ..................... 73/23.2; 73/31.06
(58) Field of Classification Search ............... 73/23.2, 73/31.06
See application file for complete search history.

(56) References Cited

U.S. PATENT DOCUMENTS 6,634,213 B1 * 10/2003 O'Connor et al. ......... 73/31.06
2003/0079999 A1 * 5/2003 Penner et al. ............. 205/775
2004/0175631 A1 * 9/2004 Crocker et al. ............. 430/5
2005/0064204 A1 * 3/2005 Lalli et al. ............... 428/428
2005/0064618 A1 * 3/2005 Brown et al. .............. 438/49
2005/0224360 A1 * 10/2005 Varghese et al. .......... 205/171

OTHER PUBLICATIONS

Dankert and Pundt, "Hydrogen-induced percolation in discontinuous films", Applied Physics Letters, vol. 81, No. 9, Aug 26, 2002.*
F. Favier, E.C. Walter, M.P. Zach, T. Benter, R.M. Penner, Science, 293, 2227 (2001).
E.C. Walter, F. Favier, R.M. Penner, Anal. Chem., 74, 1546 (2002).
T.K. Tromp, R.L. Shia, M.A. Joim, M. Eiler, Y.L. Yung, Science 300, 1740 (2003).
M.G. Schultz, T. Diehi, G.P. Brasseur, W. Zittel, Science 302, 624 (2003).
J.N. Huiberts et al., Nature 380, 231 (1996).
F. Dimeo et al., Proceedings of the 2002 U.S. DOE Hydrogen Program Review NREL/CP NREL/CP610, 32405 (2002).
Y. Sakamoto, K. Takai, I. Takashima, M. Imada, I Phys.: Condens. Matter 8, 3399 (1996).
N. Luo, G.H. Miley, A.G. Lipson, Appl. Surf Sci. 219, 167 (2003).

(Continued)

*Primary Examiner*—Hezron Williams
*Assistant Examiner*—Samir M. Shah
(74) *Attorney, Agent, or Firm*—Emrich & Dithmar, LLC

(57) ABSTRACT

A device and method of making same. The device or hydrogen detector has a non-conducting substrate with a metal film capable of absorbing hydrogen to form a stable metal hydride. The metal film is being on the threshold of percolation and is connected to mechanism for sensing a change in electrical resistance in response to the presence of hydrogen in contact with the metal film which causes an increase in conductivity.

27 Claims, 7 Drawing Sheets

OTHER PUBLICATIONS

B.M. Geerken, R. Griessen, I Phys. F: Met. Phys. 13, 963 (1983).
A.F. Hebard, R.R. Ruel, C.B. Eom, Phys. Rev. B 54, 14052 (1996).
J.L. Williams, I.L. Stone, Thin Solid Films 11, 329 (1972).
K. Sieradzki, K. Bailey, T.L.Alford, Appl. Phys. Lett. 79, 3041 (2001).
L.R.C. Pennetta, Gy. Trefan, Phys. Rev. Lett. 84, 5006 (2000).
R.H. Koch, R.B. Laibowitz, E.I. Alessandrini, J.M. Viggiano, Phys. Rev. B 32, 6932 (1985).
B. Wang, X. Xiao, P. Sheng, I Vac. Sci. Technol. B 18, 2351 (2000).
L. Schlapbach, A. Ziittel, Nature 414, 353 (2001).
R.J. Wolf, M.W. Lee, R.C. David, P.J. Fay, J.R. Ray, Phys. Rev. B 48, 12415 (1993).
T.B. Flanagan, W.A. Oates, Annu. Rev. Mater. Sci. 21, 269 (1991).
J.E. Morris, A. Kiesow, M. Hong, F. Wu, mt. I Electron 81, 441 (1996).
A. Barr, Thin Solid Films 41, 217 (1977).
F. Wu, J.E. Morris, Thin Solid Films 246, 17 (1994).
F. Favier, E.C. Walter, M.P. Zach, T. Benter, R.M. Penner, Science 293, 2227 (2001).
O. Dankert, A. Pundt, Appl. Phys. Lett. 81, 1618 (2002).

* cited by examiner

ULTRAFAST AND ULTRASENSITIVE HYDROGEN SENSORS BASED ON SELF-ASSEMBLY MONOLAYER PROMOTED 2-DIMENSIONAL PALLADIUM NANOCLUSTERS

CONTRACTUAL ORIGIN OF THE INVENTION

This work is supported by the U.S. Department of Energy (DOE), Energy Efficiency and Renewable Energy, as part of a DOE program to develop electric power technology, under Contract W-31-109-Eng-38.

FIELD OF THE INVENTION

The invention relates to devices sensitive to hydrogen and more particularly to hydrogen gas sensors fabricated from a film of mobile metal nanoclusters on the threshold of percolation.

BACKGROUND OF THE INVENTION

Hydrogen is an extremely clean energy source for use in fuel cells and internal combustion engines. However, widespread use of hydrogen as a fuel will require innovations in hydrogen storage and hydrogen sensing. Reliable, cheap, compact, and safe hydrogen sensors are needed both for measuring the hydrogen concentration in flowing gas streams and for monitoring ambient air for leaked hydrogen. It is essential that "alarm" sensors detect hydrogen at a concentration well below the lower explosion limit in air of 4%.

The vast majority of hydrogen sensors use a palladium element to selectively absorb hydrogen. Such sensors operate by detecting a change in the properties of the palladium/hydrogen solution relative to those of pure palladium. The properties detected include mass, volume, electrical resistivity, optical constants, and the work function. Conventional palladium-based hydrogen sensors, however, have two main disadvantages: First, the response time for these devices, which tends to range from several minutes to 0.5 s, is too slow to permit useful, real-time monitoring of flowing gas streams. Second, palladium is poisoned by exposure to reactive species, such as hydrocarbons, $O_2$, $H_2O$, and CO, that chemisorb on the palladium surface and block adsorption sites needed for hydrogen. These species are exactly the sorts of contaminants that are likely to be present in the gaseous feed stream supplying a fuel cell or an internal combustion engine. Exposure of a palladium-based hydrogen sensor to these gases causes the response time for the sensor to increase, and can necessitate recalibration of the sensor for hydrogen.

Today, most hydrogen gas sensors are macroscopic palladium resistor-based sensors. Exposure to hydrogen gas causes an increase in the resistance in these devices by a factor of up to 1.8 at 25° C. The resistance increase is caused by the increased resistivity of palladium hydride relative to pure palladium. Although useful, these sensors not only suffer from the disadvantages noted above, they tend to require heating to operate efficiently, which tends to result in higher power consumption.

In view of such devices, it is desirable to provide a device sensitive to hydrogen, particularly a hydrogen gas sensor that is very easy to fabricate and responds very quickly to the presence of hydrogen gas.

SUMMARY OF THE INVENTION

This invention relates to hydrogen sensitive devices and more particularly to a hydrogen sensor. More specifically this invention relates to a hydrogen sensor with a rapid response time (<1 second), ultrahigh sensitivity and to a method of making the sensor. Short response time hydrogen sensors is needed for measuring the hydrogen concentration in flowing gas streams and for monitoring ambient air for leaked hydrogen.

The ultrafast response and ultrasensitive hydrogen sensor of this invention consists of a discontinuous palladium film comprised of nanoclusters which are not or are barely connected to each other in the absence of hydrogen, on various substrates. These films are on the threshold of percolation. The hydrogen sensing of the palladium nanoclusters is based on the increase in conductance induced by the size increase of the palladium nanoclusters in the presence of hydrogen. The swelling leads to a higher electrical conductivity by increasing the number of contacts between neighboring nanoclusters. Nanocluster hydrogen sensor systems have been developed by thermally depositing a few nanometers of palladium onto flat oxide substrates such as glass or silicon dioxide that are preferably coated with a siloxane self-assembly monolayer. As palladium is deposited onto such hydrophobic flat surfaces, palladium nanoclusters with only a few nanometers intervals apart from each other spontaneously form or bead in order to reach the minimal surface free-energy. In addition, the siloxane self-assembled monolayer in between the palladium nanoclusters and the oxide substrate also reduces the palladium nanoclusters adhesion on the substrates, which significantly accelerates the swelling of the palladium nanoclusters. The response time to conductance change of palladium clusters formed by coating 6 nm palladium on a siloxane treated glass substrate, subjected to 2% hydrogen mixed with 98% nitrogen was 68 milliseconds with a remarkable conductance signal change of 100%. The inventive device can detect hydrogen concentration as low as 20 ppm (1 ppm is one part per million), i.e. 0.002% hydrogen, which is 2,000 times below the explosion limitation of hydrogen (4%).

Accordingly, an object of the present invention is to provide a device, comprising a non-conducting substrate having thereon a metal film capable of absorbing hydrogen to form a stable metal hydride, the metal film being on the threshold of percolation, and mechanism in electrical communication with the metal film for sensing a change in electrical resistance in response to the presence of hydrogen in contact with the metal film, whereby hydrogen absorbed by the metal film forms a metal hydride larger in volume than the metal resulting in percolation of the metal film and an increase in the conductivity thereof.

Another object of the present invention is to provide a hydrogen detector, comprising a non-conducting substrate having associated therewith mobile Pd or Pd alloy nanoclusters forming a film on the threshold of percolation, and mechanism in electrical communication with the Pd or Pd alloy film for sensing the change in electrical resistance in response to the presence of hydrogen in contact with the Pd or Pd alloy film, whereby hydrogen absorbed by the Pd or Pd alloy nanoclusters causes the nanoclusters to swell resulting in percolation of the Pd or Pd alloy film and an increase in the conductivity thereof.

A final object of the present invention is to provide a method of making a device, comprising providing a non-conducting substrate, depositing a metal film capable of absorbing hydrogen to form a stable metal hydride on or in association with the substrate, the metal film being on the threshold of percolation, and establishing mechanism in electrical communication with the metal film for sensing a change in electrical resistance in response to the presence of hydrogen in contact with the metal film, whereby hydrogen absorbed by the metal film forms a metal hydride larger in volume than the metal resulting in percolation of the metal film and an increase in the conductivity thereof.

BRIEF DESCRIPTION OF THE DRAWINGS

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE PREFERRED EMBODIMENT

Figure 1:
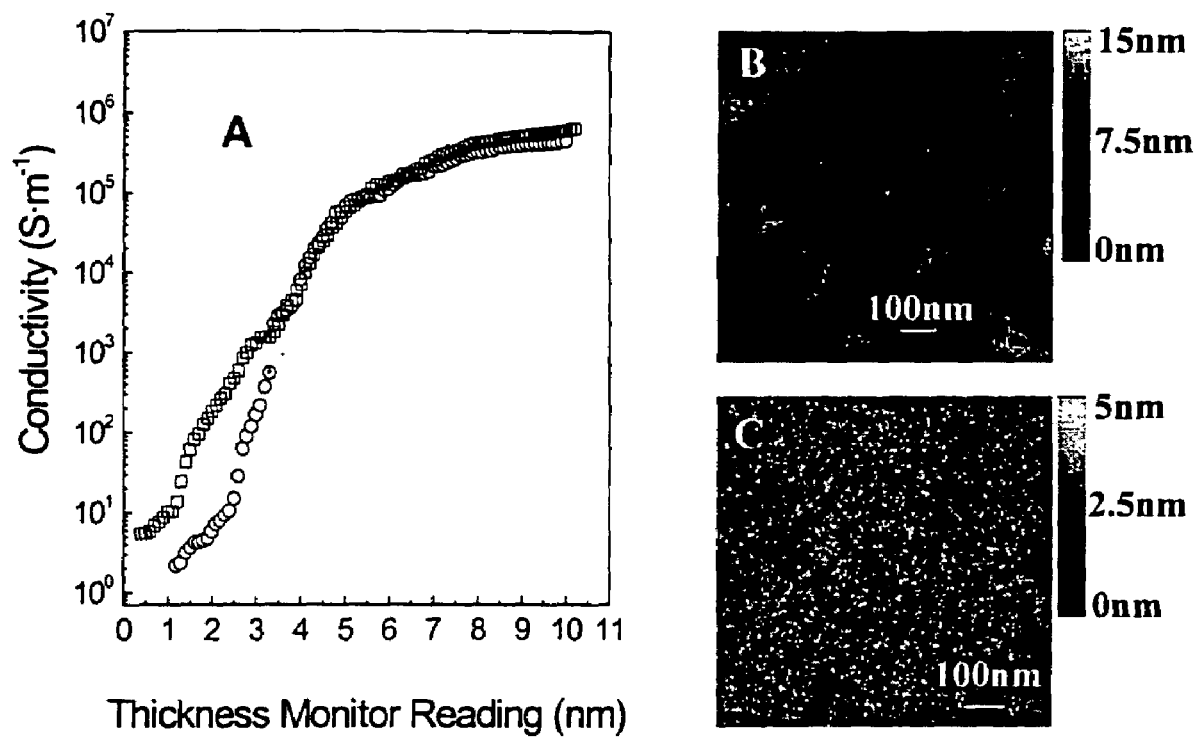
FIG. 1A is a graphical representation of the relationship between the thickness and conductivity of a film deposited on a clean glass surface and a siloxane self assembled monolayer coating glass surface.
FIG. 1B is an Atomic Forced Microscopy (AFM) of a nominal 3.3 nm Pd evaporated on a clean glass substrate.
FIG. 1C is an AFM of nominal 3.3 nm Pd evaporated on a siloxane coated glass substrate.

We investigated the transport response to hydrogen in ultrathin Pd films with nanoscopic surface structure and high surface-volume ratio, because the electronic property in ultrathin metal film can be highly surface morphology-dependent, particularly at the percolation threshold. The scattering of conduction electrons at grain boundaries or at planar interfaces defined by the top and bottom surfaces of the ultrathin film can influence significantly to the film conductivity. This invention relates to transport transition upon hydrogen adsorption in ultrathin Pd film preferably deposited on a siloxane self-assembled monolayer (SAM) coated glass. The resulting ultrathin Pd film, preferably less than about 10 nm, appears refined and densely packed Pd nanograins and exhibits reversible fast and sensitive response to the presence of hydrogen.

The device fabrication involves two steps. First, sanitized microscope cover glass pieces were immersed in 1 mM N-octyldimethylchlorosilane in a 4:1 volume mixture of hexadecane and chloroform or in commercial rain repellant for 24 hrs for the formation of siloxane SAM and rinsed with isopropanol. Ultrathin Pd was then evaporated onto the siloxane SAM coated glass and the nominal thickness was recorded by a quartz crystal microbalance. For characterization and calibration, two gold contacts (0.3 mm apart) were pre-deposited onto the two sides of the substrate and connected to the outside circuit through a vacuum feedthrough in order for in-situ measuring the conductivity of the ultrathin Pd film during its growth.

In another example, the following procedure was used to make a hydrogen sensor.

1) Microscope cover glass slips (1×1 inch, 120 micron in thickness, Gold Seal Record No. 3306) were first sanitized by 7× detergent, rinsed with D.I water and then washed with pure acetone under ultrasonication and then dried under a stream of nitrogen gas. The cover glass was then cut into 2 mm×5 mm pieces and were immersed in commercial rain repellant (Prestone, ***) or in 1 mM N-octyldimethylchlorosilane (United chemical Technology, Lot # 20400028) in a 4:1 volume mixture of hexadecane and chloroform for 24 hrs for the formation of siloxane SAM and rinsed with isopropanol. These were dried in a stream of nitrogen.

2) Two 50 nm thick gold contacts were deposited onto the substrates with a 20~300 micron wide gap across the exposed face of the glass piece.

3) Deposition of about 3.5 nm Pd (Aldrich, 99.99%, ***) were coated onto the substrate by an Polaron E6700, Turbo Vacuum Evaporator (VG Microtech), The power switch was slowly turned to level "4". The vacuum is less than 2×10−5 mbar. The distance between substrate and evaporation source is approximately 10 cm while the thickness monitor is 35o tilted from vertical direction. The 3.5 nm thickness is observed by the quartz crystal thickness monitor and the quartz crystal is newly installed. Note that the 3.5 nm is only suitable for the setup in our lab and should be recalibrated if other system will be used. This thickness on our system is the threshold for percolation as described on slide #24. The measurement by thickness monitor is really irrelevant since it depends on the thickness monitor's position, angle shielding, etc. The important parameter is being at the threshold of percolation.

4) The Pd coated glass gets glued with cyanoacrylate Pd side up onto a 5 mm×13 mm fiberglass filled printed circuit board which has simple tin coated copper lines for contacts. The two gold contacts on the Pd coated glass get connected to on the board using a small piece of indium pressed onto both the gold and printed circuit board lines. Indium in this design gives a soft but robust electrical contact. In a commercial design the Pd would be deposited directly onto a carrier substrate. The printed circuit board gives a standard geometry and is easy to handle so that testing can be completed without having to make and break delicate contacts.

Testing Process

A special cell was designed to provide continual flow of both purging and test gases with a small dead volume so accurate response times could be measured. The concentrations are set using two Aalbourg mass flow controllers and a manifold comprised of 5 solenoid valves. The final valve before the sensor delivers a purge gas of nitrogen when in the normally closed position or the pre-mixed test gas if in the open position. The response time of this valve is stated from the manufacturer as a maximum of 25 ms on and 30 ms max off. The dead volume and flow rates used give an addition 3 ms between the valve activation and the measuring of the signal. Experiments are programmed using Labview to control the valves and a Cypress Systems Omni 90 potentiostat. The interface to the computer is a National Instruments PCMCIA 6064E data acquisition card and some custom electronics. The potentiostat is programmed to apply a voltage and measure a current. The current is converted to a resistance by the relationship V=iR where V is the potential in Volts, I is the current and R is the resistance in ohms.

FIG. 1A shows the dependence of film conductivity in logarithmic scale on the nominal film thickness during the Pd evaporation onto a clean glass substrate and on a siloxane coated glass. For both of the two types of substrates, the Pd film conductivity is strongly thickness-dependent within the initial 5 nm deposition and the measurable film conductivity from 1 nm to 5 nm increased nearly five orders of magnitude. In the higher thickness region, the Pd film conductivity appears less sensitive to film thickness. In detail, a continuous increase in film conductivity is observed as Pd film grew on the clean glass and asymptotically approaches to $6.2 \times 10^5$ S·m$^{-1}$ at 10 nm nominal thickness. In comparison, for Pd film growing on a SAM coated glass, an obvious kink can clearly be identified at nominal film thickness between 3.3 and 3.4 nm, which distinguishes it from the clean glass. Within this nominal thickness growth of 0.1 nm, the conductivity of the film increased by a factor of 45. Above this critical thickness, the two curves starts to converge in higher thickness region. The surface morphology of the two types of samples at the critical thickness of 3.3 nm is also shown with atomic force microscopy (AFM). Evaporated Pd wets the clean glass surface and forms randomly connected Pd domains with averaged size of 1,200 nm$^2$, about 6 nm in height and approximately 100 nm apart from each other as seen in FIG. 1B. In contrast, 3.3 nm Pd on siloxane SAM coated glass as seen in FIG. 1C appears as much denser and refined Pd nanoclusters. We believe that the onset kink at ~3.3 nm in FIG. 1A indicates the film is on the threshold of percolation as shown in FIG. 1C, on which further added Pd atoms begin to fill the boundary and drastically enhance the metallic conduction between neighboring grains. The increased surface free energy between siloxane SAM and Pd significantly reduces the size of the deposited Pd grains accompanied by the increased grain density in order to balance the total materials. The direct consequence is that the total amount of the boundaries between the Pd grains increases and the width of the boundary between the grains gets narrowed. The average width of grain boundary in the Pd ultrathin film on siloxane SAM is below 10 nm while that for Pd on clean glass is around 100 nm.

Figure 2:
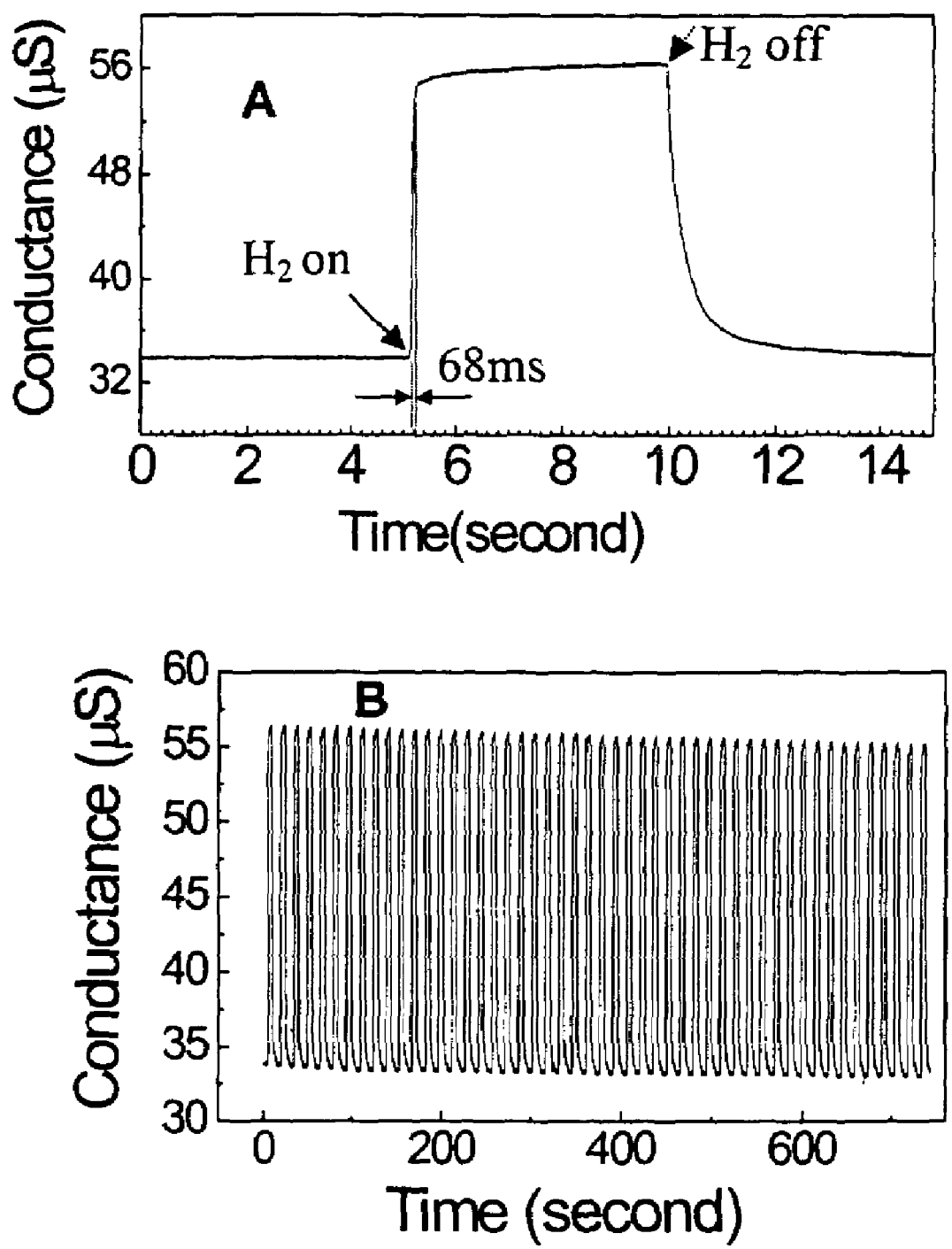
FIG. 2A is a graphical representation of the relationship between conductance and elapsed time for a 3.3 nanometer Pd film on SAM siloxane in a 2% hydrogen and nitrogen mixture.
FIG. 2B is a plot of 50 exposures to hydrogen of the sample used in FIG. 2A.

Opposite to the response of a bulk Pd resistor to H$_2$, the conductance of a ultrathin Pd film on siloxane SAM increased 65% in the presence of 2% H$_2$, as seen in FIG. 2A. The corresponding rise-time (baseline to 90% signal saturation) of approximately 70 ms has been observed for the response of the film to 2% H$_2$, a concentration below the hydrogen explosion range of 4%–75% for effective early-alarming. In addition, the conductance signal intensity and the rising time undergo negligible changes after being repeatedly exposed to 2% H$_2$, as seen in FIG. 2B. It is known that the conductivity of macroscopic PdHx reaches a minimum at x~0.7, with a surprising rise following at the further increase of x, presumably due to the further electron filling by hydrogen to the 6-th d-band of Pd more than offsets the loss in the hole number and the net effect is the increase in total number of charge carriers, i.e electron. However, such rise in conductivity never exceeds the conductivity of pure Pd while the observed increase in conductance in the present invention is relative to pure Pd. Therefore, a different mechanism must operate in the SAM-supported ultrathin Pd film at percolation threshold.

Figure 3:
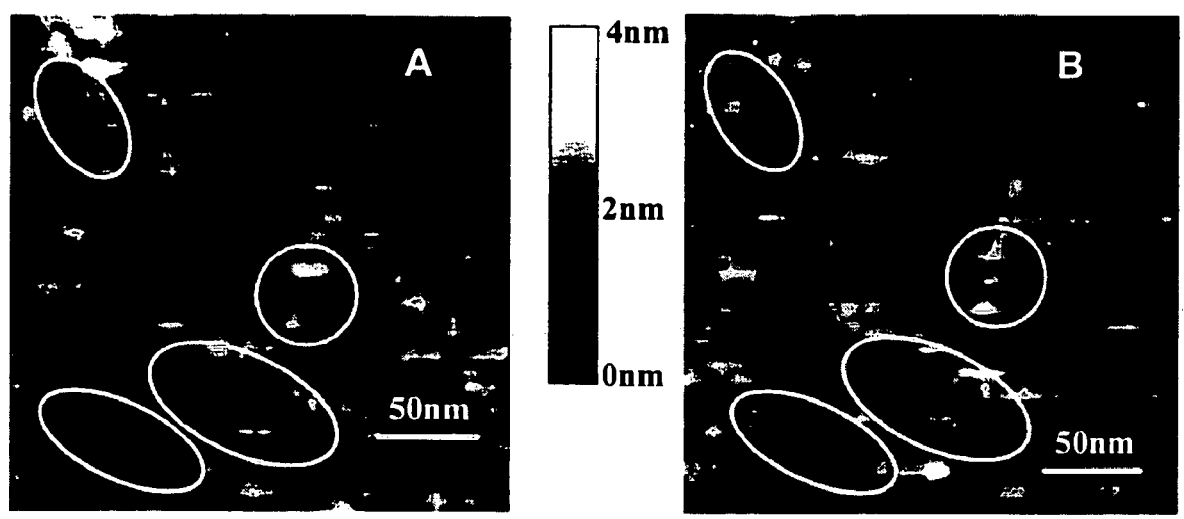
FIG. 3A is an AFM image of a 3.3 nm on a SAM siloxane coated glass.
FIG. 3B is an AFM image of the same glass illustrated in FIG. 3A in a hydrogen gas atmosphere.

In-situ AFM studies is revealed that under a stream of hydrogen, the grain-boundaries in the Pd film tend to heal and the bearing film volume within the scanning area swelled ~7%, as seen in FIG. 3A. It is also known that hydrogen atoms can diffuse into the FCC Pd cluster that leads to the dilation of Pd lattice. At room temperature, the lattice constant of fcc Pd is 3.889 Å, whereas that for stable β-phase PdH$_{0.7}$ is 4.025 Å—an increase of 3.5%, corresponding to 11% increase in volume. Therefore, it is believed that the healing of the grain-boundary in Pd nanocluster film is caused by the dilation of the individual Pd nanograins, which in turn, leads to a higher electrical conductance by the increasing number of contacts between neighboring Pd nanograins. Such hydrogen-induced conductivity of Pd film increase is maximized when film thickness is at percolation threshold, which can be characterized by the plot of film conductivity versus film thickness.

The siloxane SAM in between the Pd layer plays crucial dual-roles. Siloxane SAM modifies the surface morphology of the coated Pd film, which considerably reduces the inter-distance between neighboring grains, increases the amount of the grain boundary and substantially enhances the conductivity variation at percolation threshold as indicated by the comparison between FIG. 1A and FIG. 1B. In addition, siloxane SAM also alleviates the stiction between Pd nanograins and the glass substrate, which is so strong that even hydrofluoric acid is failed to strip Pd film off a glass substrate.

Figure 4:
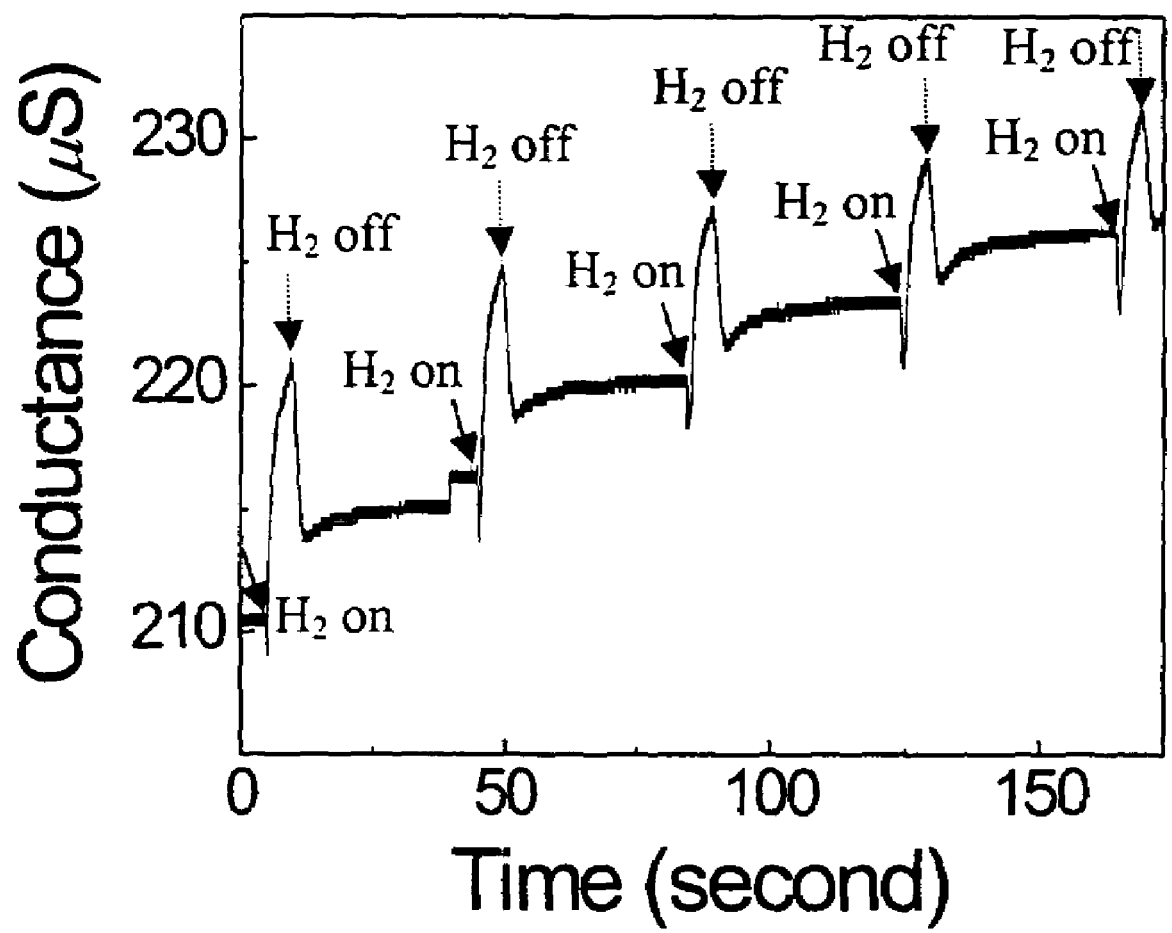
FIG. 4 is a graphical representation of the relationship between conductance and time for a 3.3 nm Pd film deposited on a clean glass substrate with a 2% hydrogen and nitrogen mixture.

As described above, the adsorption of hydrogen by Pd can have two opposing effects on the transport properties of Pd thin film, that is, decreasing the film conductance by the formation of PdH$_x$ and increasing the film conductance by healing of the grain boundary in the film. The competition of these two opposing effect can be observed in samples of thin Pd film deposited on clean glass, as seen in FIG. 4. The initial drop in conductance ascribed to the formation of Pd hydride is offset and eventually outpaced by a rising conductance due to Pd cluster swelling. For these samples, the events sequence during conductance variation always starts with a decrease followed by an increase in conductance, while inversed events sequence has never been observed.

According to the scaling relation for percolation disorder, the conductivity R for percolating systems can be written by the scaling law C~|P−P$_c$|$^\tau$, where P is the surface fraction of conducting, Pc is the critical value of p corresponding to the percolation threshold, and is the conductivity exponent ( ). Assuming the conducting population decrease linearly in time during the desorption of hydrogen, the conductance of film at percolation threshold can be expressed as C~|t−t$_f$|$^\tau$, where t$_f$=t(P$_c$) is the filling time.

Figure 5:
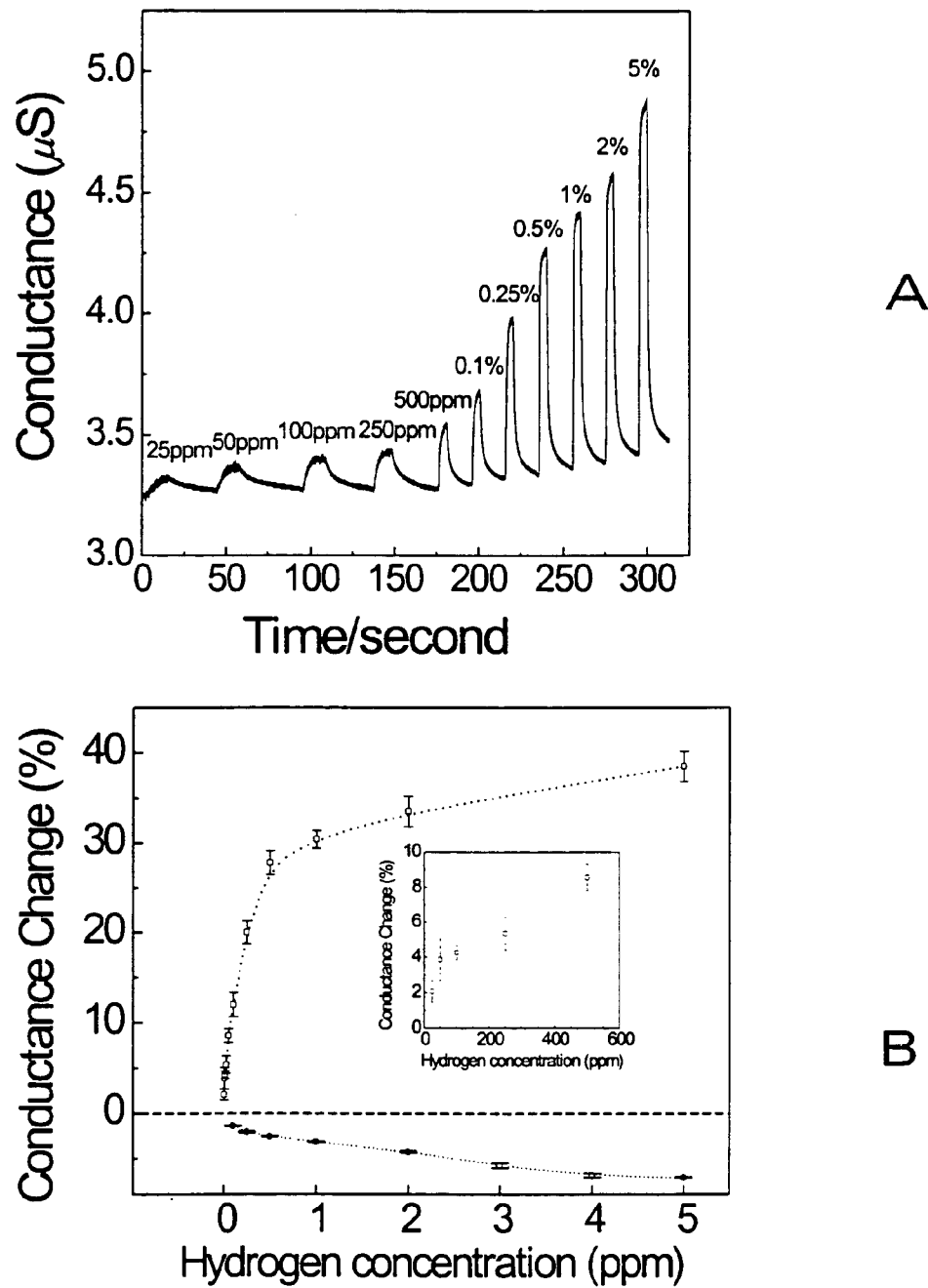
FIG. 5A is a sensitivity plot showing the relationship of a single 3.3 nm Pd on siloxane SAM for various concentrations of hydrogen with the balance being nitrogen.
FIG. 5B is a plot like FIG. 5A showing the comparison of conductance change and percentage versus the hydrogen concentration in percentage for a 3.3 nm thick palladium film on a SAM monolayer and a 10 nm Pd film on a SAM monolayer.

The dual-effect brought by the siloxane SAM yields the H$_2$ detecting ability of the device as sensitive as to 25 ppm, as seen in FIG. 5A. The sensor exhibited a sigmoidal response curve, as seen in FIG. 5B by increased conductance to hydrogen. Inversely, a sensor based on 10 nm thick Pd film on siloxane SAM, whose conductivity is near inert to film thickness, see FIG. 1, shows less sensitivity to the presence of hydrogen by decreased conductance, as seen in FIG. 5B.

Figure 6:
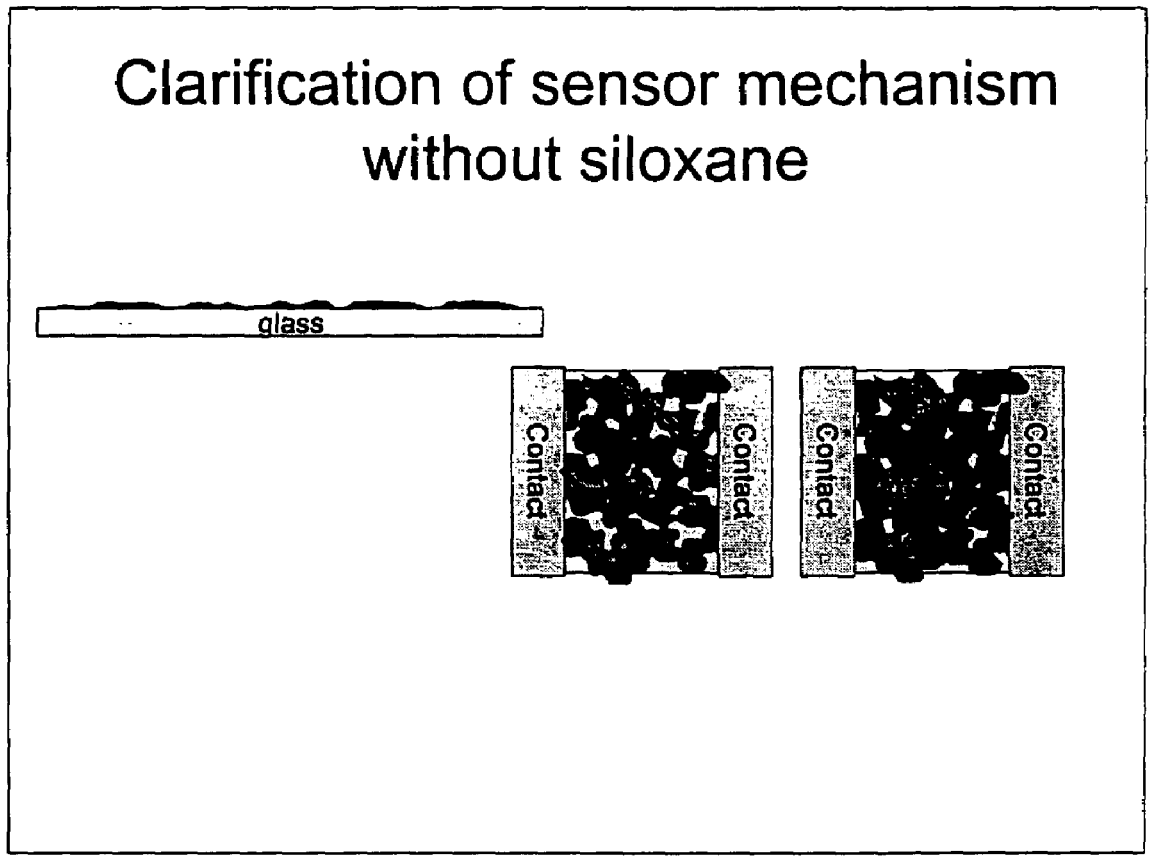
FIG. 6 is a representation of electron conductive paths in a unmodified glass having Pd grains deposited thereon.

Referring now to FIG. 6, there is illustrated a representation of the effect of depositing nanometer grains of Pd on an unmodified glass substrate. Without this siloxane or other low free surface energy surface, the number of conductive paths will be the same but the resistivity increases when hydrogen is present, thus making a sensor or device with less conductivity. The expansion of Pd grains that are already touching may make some conductive paths rupture and will contribute to the irreversibility of some sensors due to the rupturing or defamation of some conductive paths. A device made in accordance with FIG. 6, would be useful in determining whether hydrogen was ever present in the atmosphere to which a sensor made in accordance with FIG. 6 was exposed, since the reaction here is not as reversible or irreversible with respect to devices made as illustrated in FIG. 7.

Figure 7:
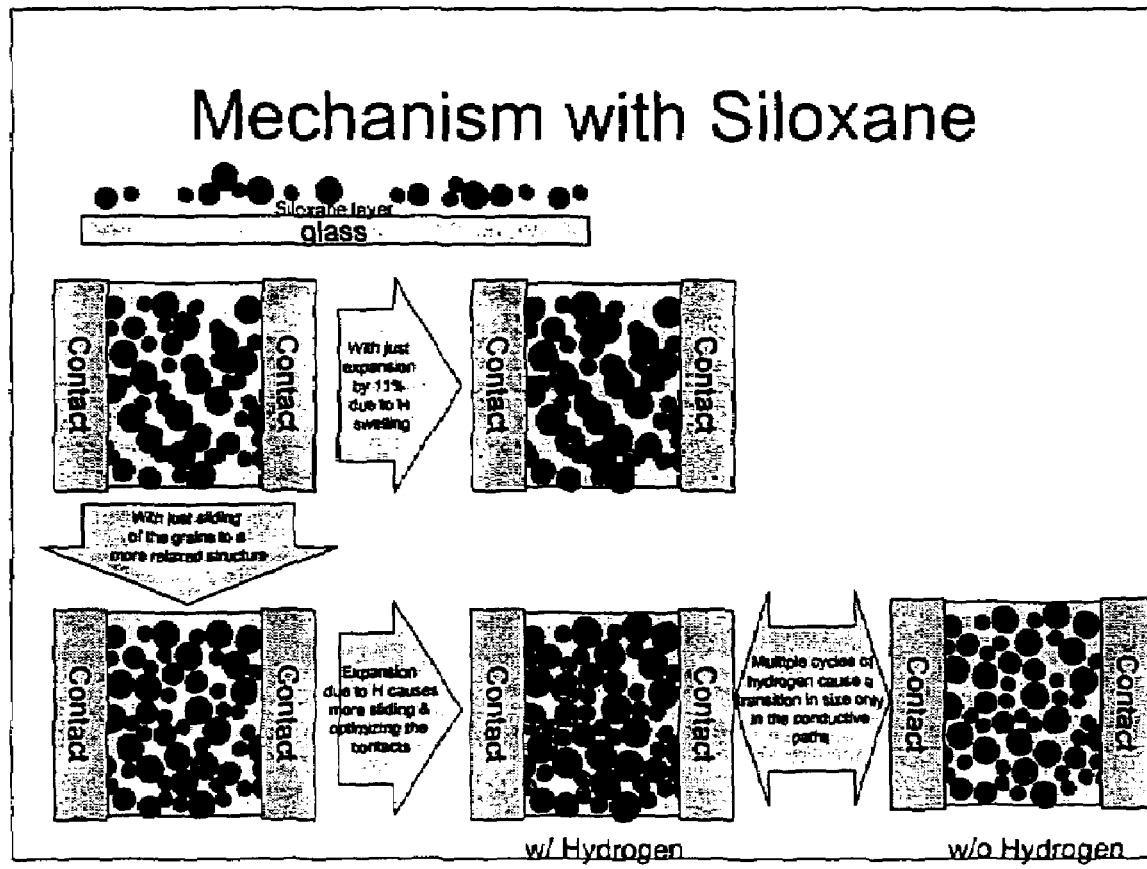
FIG. 7 is a representation of the glass of FIG. 6 with a siloxane layer showing the affect thereof with Pd beads formed thereon.

Referring now to FIG. 7, there is illustrated the mechanism in which a modification of a glass surface is provided wherein a stiction-reducing surface or coating is on the substrate, for instance a siloxane layer and most preferably, a siloxane monolayer. Alternatively, the substrate may have a hydrophobic surface, as will be described, but in any event, as seen, Pd deposited on such a device forms beads rather than forming a bond with the substrate. It is believed that siloxane which provides low surface free energy is responsible for the beads forming and this is extremely important because the beads are therefore more mobile in the device of FIG. 7 than in the device of FIG. 6 so that when hydrogen is introduced the beads swell and are able to assume new positions that are optimized to provide a maximum number of contacts thereby increasing the electrical conductivity greatly as opposed to the device shown in FIG. 6.

Although the device has been principally described with respect to a hydrogen detector, there may be other uses for such a device such as switches and other devices. It is intended to cover in the claims appended hereto all such devices.

As previously stated, the Pd nanoclusters may have an average diameter of less than about 10 nanometers and the film thickness may also be and is preferably less than about 10 nanometers and most preferably less than about 5 nanometers. In the particular chamber used to deposit the films of the subject invention as described hereinbefore, films of 3.3 to 3.4 nm showed superior sensitivity but that is a function of the geometry of the electrodes and substrate and the chamber in which the films were made and it is understood by one of ordinary skill in the art that devices have to be calibrated depending upon a variety of factors used in the production thereof.

The substrate maybe any suitable material, but preferably has low surface free energy. In addition, the substrate itself or the surface thereof may be hydrophobic or the hydrophobic characteristic may be due to a coating on the substrate. Available substrates are glass, silicon, various polymers, polypropylene, fluorinated polyethylene, or wax. This list is not exhaustive but only representative.

The metal film preferably is in the form of mobile metal nanoclusters but in the case of untreated glass or other surfaces with higher free surface energy the nanoclusters may be less mobile and be used to provide a different type of sensor or device.

Referring to siloxane self assembled layers, preferably a siloxane self-assembled monolayer is used and by monolayer we mean substantially monolayer between it may be at least portions of the self assembled layer is not a monoloayer. Moreover, preferably, the siloxane is an alkylsilane and may contain fluorine atoms for instance such as undecyltrichlorosilane or the alkylsilane may contain chlorine atoms for instance octadecyl trichlorosilane. Other silanes such as alkylsilanes which are useful in the present invention are carboxyterminated alkylsilanes.

The metal film of nanoclusters maybe one or more of Pd, Cu, Au, Ni, Rh, Pt, Y, La or alloys thereof and most preferably is Pd or alloys thereof. As used in the claims herein, the term "non-conducting substrate" means a non-electrically conducting substrate although the substrate may be an ion conducting substrate.

While there has been disclosed what is considered to be the preferred embodiments of the present invention, it is understood that various changes in the details may be made without departing from the spirit, or sacrificing any of the advantages of the present invention.

The embodiments of the invention in which an exclusive property or privilege is claimed are defined as follows:

1. A device, comprising a non-conducting substrate having thereon, a metal film comprised of nanoclusters of metal atoms capable of absorbing hydrogen to form a stable metal hydride, said metal film being on the threshold of percolation, and mechanism in electrical communication with said metal film for sensing a change in electrical resistance in response to the presence of hydrogen in contact with said metal film, whereby hydrogen absorbed by said metal film forms a metal hydride larger in volume than the metal resulting in percolation of said metal film and an increase in the conductivity thereof; and wherein said non-conducting substrate has a stiction-reducing coating thereon.

2. The device of claim 1, wherein said metal nanoclusters have an average diameter of less than about 10 nanometers.

3. The device of claim 1, wherein many of said metal nanoclusters are mobile with respect to each other.

4. The device of claim 3, wherein non-conducting substrate has a self-assembled layer thereon.

5. The device of claim 4, wherein said non-conducting substrate has a siloxane coating thereon which is substantially a monolayer.

6. The device of claim 5, wherein the siloxane is an alkylsilane.

7. The device of claim 6, wherein the alkylsilane contains chlorine atoms.

8. The device of claim 7, wherein the silane is octadecyl trichlorosilane.

9. The device of claim 5, wherein the alkylsilane contains fluorine atoms.

10. The device of claim 9, wherein the alkylsilane is fluorinated undecyl trichlorosilane.

11. The device of claim 4, wherein the self-assembled layer is a carboxy terminated alkylsilane.

12. The device of claim 1 wherein said non-conducting substrate has a hydrophobic surface.

13. The device of claim 1 wherein said metal film on the threshold of percolation has a thickness of less than about 10 nm.

14. The device of claim 1 wherein said metal film on the threshold of percolation is less than about 5 nanometers thick.

15. The device of claim 1 wherein said metal film on the threshold of percolation is between 3.3 and 3.6 nanometers thick.

16. The device of claim 1, wherein said metal film is one or more of Pd, Cu, Au, Ni, Rh, Pt, Y, La or alloys thereof.

17. The device of claim 1, wherein said metal film is Pd or an alloy thereof.

18. A method of making a device, comprising providing a non-conducting substrate with a coating thereon having a low surface free energy, depositing a metal film capable of absorbing hydrogen to form a stable metal hydride on or in association with the substrate, the metal film being on the threshold of percolation, and establishing mechanism in electrical communication with the metal film for sensing a change in electrical resistance in response to the presence of hydrogen in contact with the metal film, whereby hydrogen absorbed by the metal film forms a metal hydride larger in volume than the metal resulting in percolation of the metal film and an increase in the conductivity thereof.

19. The method of claim 18, wherein the substrate surface has low surface free energy.

20. The method of claim 18, wherein the substrate is hydrophobic.

21. The method of claim 18, wherein the metal film includes mobile metal nanoclusters.

22. The method of claim 21, wherein the metal nanoclusters are one or more of Pd, Cu, Au, Ni, Rh, Pt, Y, La or alloys thereof.

23. The method of claim 22, wherein the metal nanoclusters are Pd or alloys thereof.

24. The method of claim 23, wherein the substrate has a self assembled siloxane layer thereon.

25. The method of claim 24, wherein the self assembled layer is substantially a monolayer.

26. The method of claim 25, wherein the metal film has a thickness less than about 10 nanometers.

27. A device, comprising a non-conducting substrate having thereon a non-metallic material intermediate said substrate and a metal film formed of nanoclusters of metal atoms capable of absorbing hydrogen to form a stable metal hydride, said metal film being on the threshold of percolation, and mechanism in electrical communication with said metal film for sensing a change in electrical resistance in response to the presence of hydrogen in contact with said metal film, whereby hydrogen absorbed by said metal film forms a metal hydride larger in volume than the metal resulting in percolation of said metal film and an increase in the conductivity thereof; and wherein said non-conducting substrate has a stiction-reducing coating thereon.

* * * * *